(12) United States Patent
Aboff (10) Patent No.: US 10,413,686 B2
(45) Date of Patent: Sep. 17, 2019

(54) COLUMELLA NASAL CLIP / DILATOR FOR AROMATIC SUBSTANCES

(71) Applicant: Clifford S. Aboff, Brooklyn, NY (US)

(72) Inventor: Clifford S. Aboff, Brooklyn, NY (US)

( * ) Notice: Subject to any disclaimer, the term of this patent is extended or adjusted under 35 U.S.C. 154(b) by 0 days.

(21) Appl. No.: 16/166,975

(22) Filed: Oct. 22, 2018

(65) Prior Publication Data

US 2019/0054263 A1 Feb. 21, 2019

(51) Int. Cl.

| | | |
|---|---|---|
| *A61M 15/08* | (2006.01) | |
| *A61M 29/00* | (2006.01) | |
| *A61M 21/02* | (2006.01) | |
| *A61F 5/08* | (2006.01) | |
| *A61L 9/00* | (2006.01) | |
| *A61L 9/012* | (2006.01) | |
| *A61L 9/12* | (2006.01) | |
| *A62B 9/06* | (2006.01) | |
| *A61M 21/00* | (2006.01) | |

(52) U.S. Cl.
CPC ............. *A61M 15/085* (2014.02); *A61F 5/08* (2013.01); *A61L 9/00* (2013.01); *A61L 9/012* (2013.01); *A61L 9/12* (2013.01); *A61M 21/02* (2013.01); *A61M 29/00* (2013.01); *A62B 9/06* (2013.01); *A61M 2021/0016* (2013.01)

(58) Field of Classification Search
CPC .... A61M 15/085; A61M 21/02; A61M 29/00; A61M 2021/0016
See application file for complete search history.

(56) References Cited

U.S. PATENT DOCUMENTS

| | | | |
|---|---|---|---|
| 2010/0147300 A1* | 6/2010 | Lorenzati | A61M 15/0028 128/204.14 |
| 2017/0119571 A1* | 5/2017 | Pepper | A61M 29/00 |
| 2017/0273626 A1* | 9/2017 | MacDonald | A61B 5/0002 |
| 2018/0064892 A1* | 3/2018 | Nelson | A61M 15/08 |

* cited by examiner

*Primary Examiner* — Imani N Hayman
(74) *Attorney, Agent, or Firm* — Michael J. Feigin, Esq.; Feigin and Fridman LLC (57) ABSTRACT

A nasal clip and/or dilator which is U-shaped having protruding wider spherical/spheroid holders at each end of the U is designed to be placed such that each spherical holder is in a nostril. The U-shaped clip can press against the columella and each holder against the septum. Inside each holder is a scented piece, such as a plastic ball or cylinder with aromatic compounds there-in which exit from the surface of the respective scented piece. To facilitate the scent escaping from the scented piece and into the nose, each holder has portals such as around the circumference thereof and/or on opposite sides thereof, transverse to the "U" of the holder.

17 Claims, 8 Drawing Sheets

COLUMELLA NASAL CLIP / DILATOR FOR AROMATIC SUBSTANCES

FIELD OF THE DISCLOSED TECHNOLOGY

The disclosed technology relates to nasal clips, and more particularly to a nasal clip that increases airflow in the nose and/or effuses the scent of aromatic substances for aroma therapy uses.

BACKGROUND

Various aromas and medications improve smell and give relief from nausea or queasiness in people such as pregnant women with morning sickness, people undergoing chemotherapy, or HIV treatments, people with colds and allergies, people prone to motion sickness, people exposed to noxious odors, people with hyper-sensitive smell, and others.

Aroma therapy is the practice of using volatile plant oils or essential oils for psychological and physical well being. Essential oils are the pure essence of a plant that is generally distilled from leaves, stems, flowers, bark, roots, or other elements of a plant. It is believed that the aroma of the natural essential oil stimulates the brain to trigger a reaction. Aroma therapy will not cure serious illnesses such as cancer or aids, however, it can help enhance a patient's quality of life by enhancing the patient's mood, as well as easing nausea. Aroma therapy is practiced through diffusing oils in various methods. There are many diffusers out on the market today. Examples are steamers, candles, clay pots, lamp rings, etc. All of these products have one disadvantage in common. They diffuse the scent of the oil into a room or area in a manner that effects everyone in the vicinity.

Further, breathing and airflow while one is congested or when one sleeps is a problem for many. Sleep apnea retainers, breathing masks, medications, nasal sprays and nasal dilators are often used to decrease nasal congestion, decrease snoring and allow for increased airflow in the nose. Nasal dilators in specific are devices intended to provide temporary relief from transient causes of breathing difficulties resulting from structural abnormalities and/or transient causes of nasal congestion associated with reduced airflow (21 VFR 874.3900).

As a consequence of the foregoing situation, there has existed a longstanding need among for a new and improved device for practicing aroma therapy and/or providing nasal dilation.

SUMMARY OF THE DISCLOSED TECHNOLOGY

A nasal clip/dilator which applies pressure to a columella of a user, in embodiments of the disclosed technology, has a U-shaped base with a pair of free ends disposed to grippingly engage a nasal septum. Two spheroid holders, one disposed at each end of the U-shaped base, has an (aromatic) scented piece secured therein. An aromatic substance is inhalable through the user's nasal passages during breathing when the nasal clip is worn. The spherical holders further have at least two oppositely disposed portals such that unobstructed passages are created between the scented piece and the respective nasal passages when the nasal clip is worn. The base is adapted to press the columella of said user.

A plurality of circumferential spaced portals open into each of the respective two spheroid holders further exposing the scented piece to the nasal passages in embodiments of the disclosed technology. Each scented piece is fictionally secured in a respective spheroid holder in some embodiments. This securing can be permanent in that removal of the scented pieces ordinarily requires destruction of the holder it is in. As such, "permanent" is defined as "created to remain as such during use of the device and where removal thereof requires a destructive and non-reversible act except by extraordinary means such melting and reforming."

Described another way, a nasal clip of embodiments of the disclosed technology has a top side, a bottom side, a front side, and a rear side. The sides are arbitrary with respect to the gravitational pull of the Earth, but it should be understood that the top side and bottom side are opposite to each other as are the front and rear side. The front and rear side are situated between and traverse to the top and bottom side and vice versa. Two separate spheroid holders are spaced apart and extend to the top side (or top most edge of the device). A U-shaped base connecting the spheroid holders is on an opposite bottom side (or extends to a bottom most edge of the device). The spheroid holders bulge outwards into the front and rear planes compared to the U-shaped holder, in embodiments of the disclosed technology with a circular portal in one or both of the front side and the rear side (e.g. extreme front and/or rear sides of the device) of each spheroid holder.

The "spheroid holder" is defined as "spheroid" because at least two pathways are continuous to form a circular projection around which are the framework of a sphere. in some embodiments, each spheroid holder has a spherical side which is cut into by portals and the front and back ends thereof are flattened with a circular or other portal therein. This is akin to the Earth, if it were a perfect sphere, have a line of latitude used to lop off the North and South pole with lines of longitude used to cut in side portals extending towards but not all the way to the poles, creating side portals.

The circular portal is in both of the front side and the rear side of each spheroid holder in some embodiments of the disclosed technology. Each circular portal terminates a spherical side of one of the spheroid holders and is planar with one of the front side or the rear side in embodiments of the disclosed technology. Each of the two separate spheroid holders has additional portals opening into the spherical side thereof in some embodiments of the disclosed technology. Scented pieces fill a space circumscribed by each spheroid holder (one scent ball per holder) substantially or fully filling an interior space defined by an inner most continuous wall of the respective holder. The scented pieces can further extend outwards past the inner most and/or outer most continuous wall, such as bulging out of the circular portals at each front/back end of such a spherical holder. The spheroid holder or holders, in embodiments of the disclosed technology, lack scent, and specifically, aromatic scent which is present in the scented pieces.

Adjacent sides of the two separate spheroid holders are solid and the additional portals are situated on non-adjacent sides of the two separate spheroid holders in some embodiments of the disclosed technology. The U-shaped base is adapted to be placed and/or press against a columella of a nose and each of the two separate spheroid holders against a septum of the nose in embodiments of the disclosed technology.

One can use the nasal clip by obtaining one with a pre-inserted aromatic scented piece in each of two separate spheroid holders and placing same into his or her nostrils (one spheroid holder per nostril). The U-shaped base can be abutted or press against a columella (bottom side of the nose between the two nostrils). The abutting or pressing can be on either lateral side such that the nasal clip pushes in a medial direction, opening the nostrils.

Described yet another way, the technology includes a U-shaped base whose ends open out into spaced apart spherical ends having flat front and back sides and a plurality of portals within each spherical end adapted for escape of scent from an aromatic scented piece permanently held within each of the spherical ends. The device can be sized such that the U-shaped base is adapted to abut or press a columella of a nose when each spherical end is pushed into a nostril. Breathing through a nose causes scent to be pulled from at least one of the scented piece in embodiments of the disclosed technology.

"Substantially" and "substantially shown," for purposes of this specification, are defined as "at least 90%," or as otherwise indicated. Any device may "comprise" or "consist of" the devices mentioned there-in, as limited by the claims.

It should be understood that the use of "and/or" is defined inclusively such that the term "a and/or b" should be read to include the sets: "a and b," "a or b," "a," "b."

DETAILED DESCRIPTION OF EMBODIMENTS OF THE DISCLOSED TECHNOLOGY

A nasal clip which is U-shaped having protruding wider spherical/spheroid holders at each end of the U is designed to be placed such that each spherical holder is in a nostril. The U-shaped clip can press against the columella and each holder against the septum. Inside each holder is a scented piece, such as a plastic ball/cylinder with aromatic compounds there-in which exit from the surface of the respective scented piece. To facilitate the scent escaping from the scented piece and into the nose, each holder has portals such as around the circumference thereof and/or on opposite sides thereof, transverse to the "U" of the holder.

Embodiments of the disclosed technology will become more clear in view of the following description of the figures.

Figure 1:
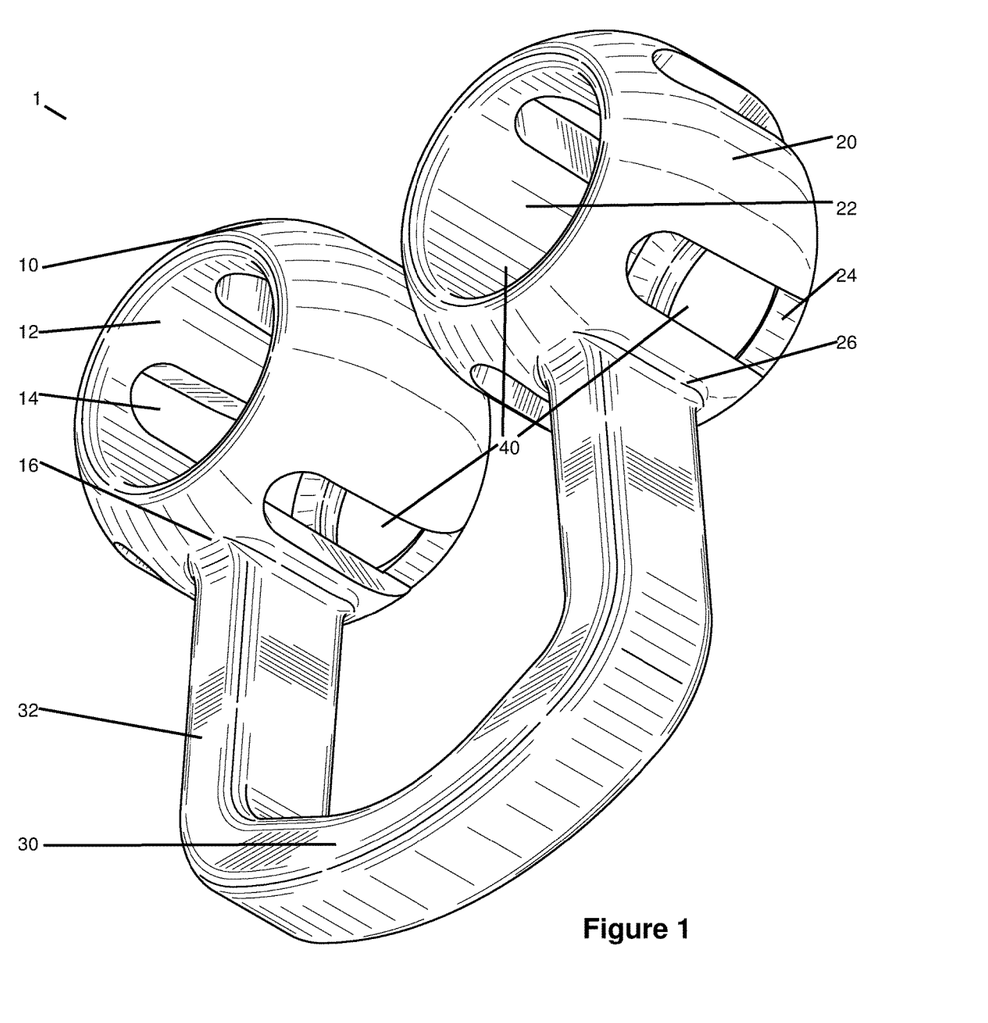
FIG. 1 shows a perspective view of a nasal clip of an embodiment of the disclosed technology.

FIG. 1 shows a perspective view of a nasal clip 1 of an embodiment of the disclosed technology. The spheroid holders 10 and 30 (with the lines pointing to an outer side thereof) have partially spherical exterior sides which are broken by front side and back side portals 40. The front side and back side portals 40 "lop off" or cut along a longitudinal line of the spheres forming circular openings. The sides also have one or more portals such as portals 14 and 24 which form openings into exterior spherical sides of the spheroid holders 10 and 20, respectively. A U-shaped connector 30/32/34 has a middle region 30 which curves into side regions 32 and 34. The extreme ends of the side regions 32 and 34 form a unitary structure with respective spheroid holders 10 and 20 at connecting regions 16 and 26, respectively. At connecting regions 16 and 26 the cross-sectional size of the nasal holder expands such that each spherical holder is wider on all sides than the U-shaped connector 32/34 in embodiments of the disclosed technology. In this manner, when pushed up into nasal cavities the U-shaped connector side regions 32 and 34 are unobstructive and one can press the middle region 30 of the U-shaped connector against the bottom of the nose between each nostril, e.g. against the columella. The inner walls 12 and 22 of each spheroid holder 10 and 20, respectively, can also form part of a sphere in embodiments of the disclosed technology.

Figure 2:
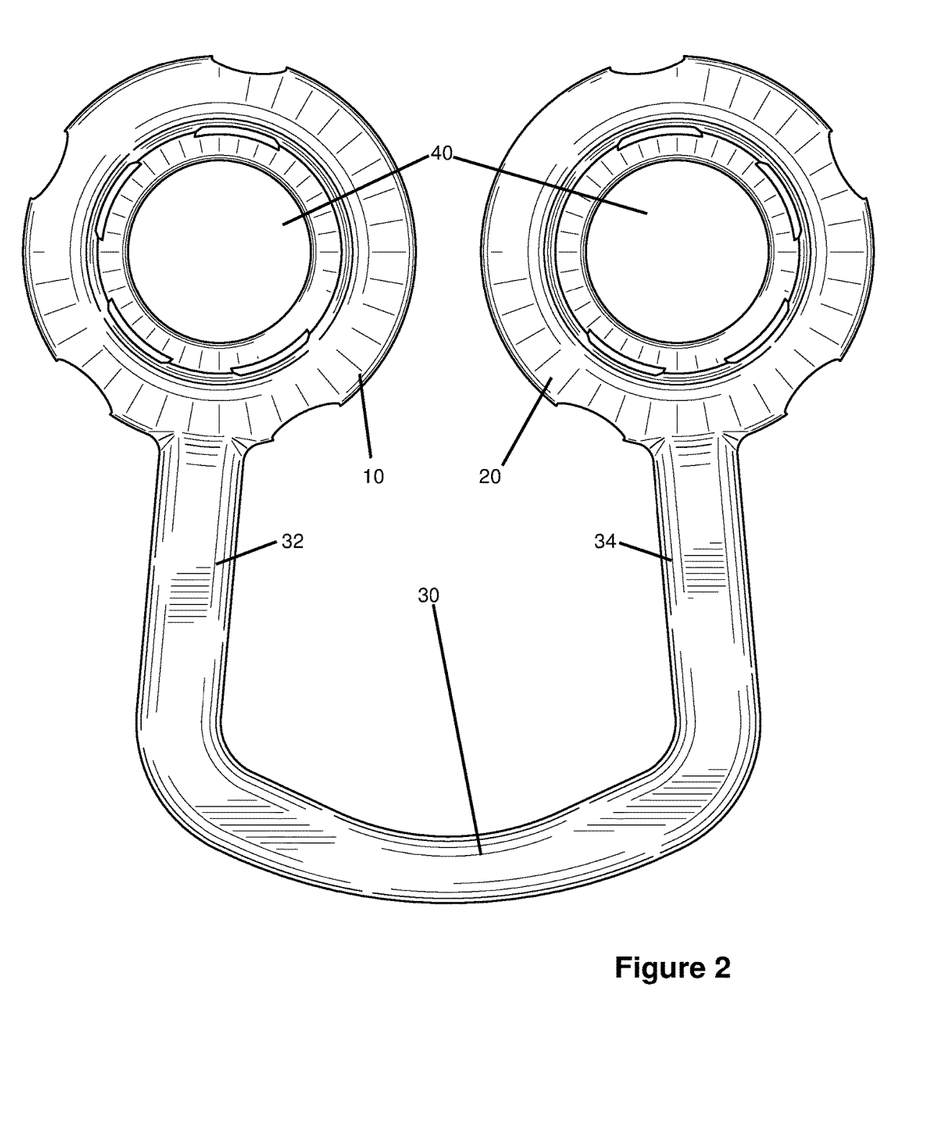
FIG. 2 shows a front plan view of the nasal clip of FIG. 1.

FIG. 2 shows a front plan view of the nasal clip of FIG. 1. In this view one can see the symmetry of the device itself, mirrored along the center of the middle region 30 of the U-shaped connector. One can also see to an extent symmetry in the transverse direction such that a plane under the paper and parallel thereto can split the connector equally in half. Further, the portals 40 on the front and back side of each spheroid holder 10 and 20 are identical in embodiments of the disclosed technology, so when lacking a scented piece one can see straight through from one side to the other.

Figure 3:
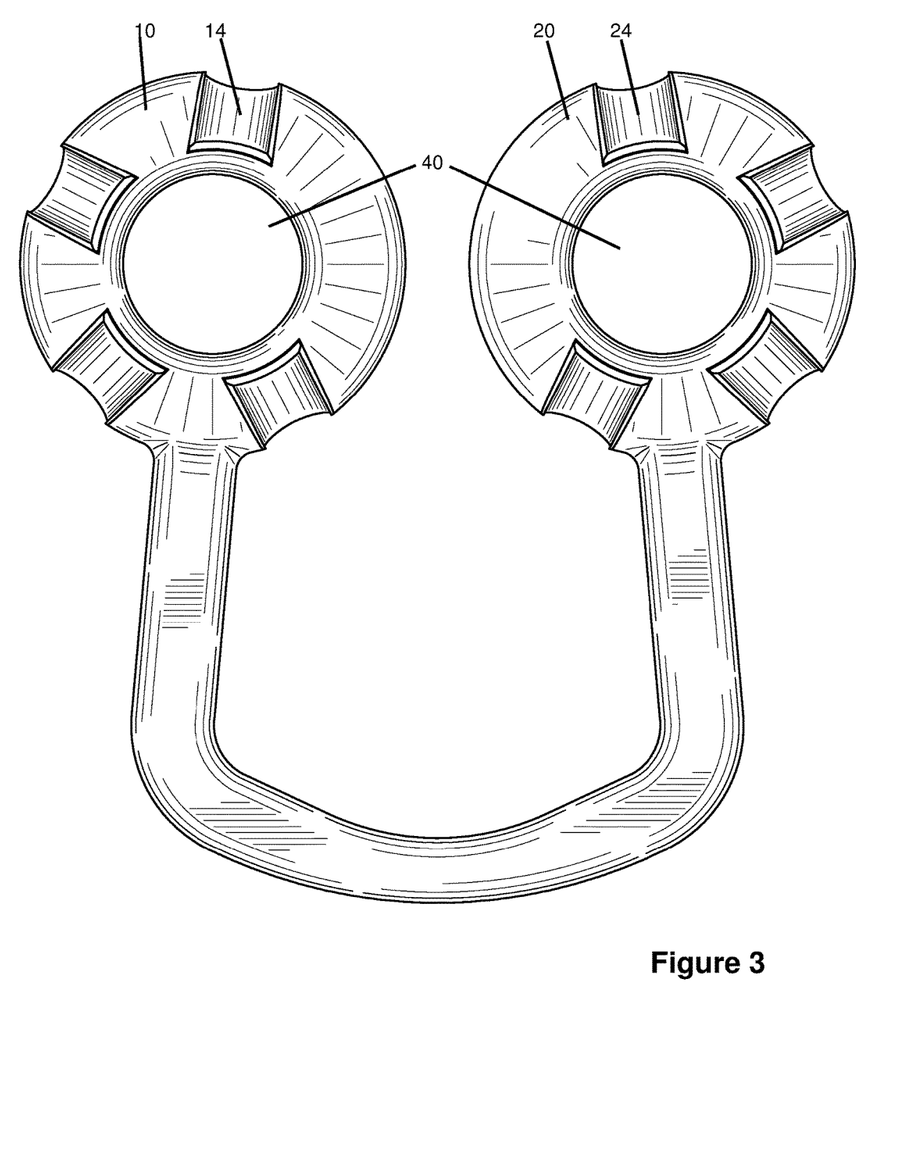
FIG. 3 shows a rear plan view of the nasal clip of FIG. 1.

FIG. 3 shows a rear plan view of the nasal clip of FIG. 1. Here, the side portals 14 and 24 are visible. It should be understood that this refers to each side portal though only one side portal is numbered in each figure.

Figure 4:
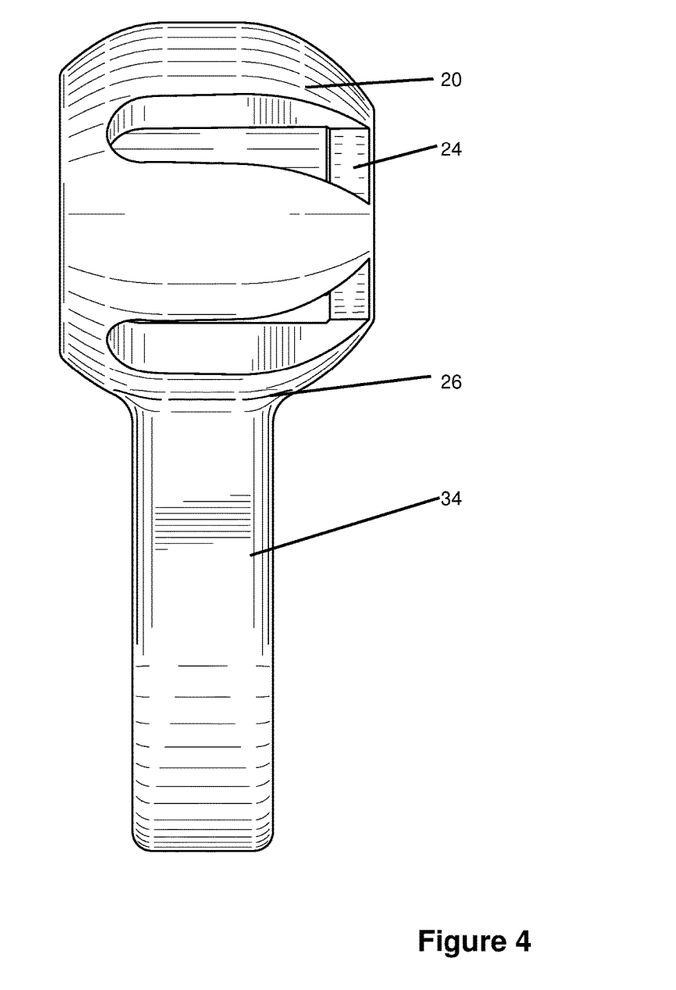
FIG. 4 shows a side view of the nasal clip of FIG. 1.

FIG. 4 shows a side view of the nasal clip of FIG. 1. The exterior side of one of the spheroid holders 20 is shown prominently in this figure. One can further see into the side portals 24, showing the interior of the spheroid holder and it's inner wall 22. At the bottom of the spheroid holder 20 is a connecting region 26 where the spheroid shape turns into a rectangular, curvilinear, and/or flat-sided top edge and remainder of the side 34 of the connector.

Figure 5:
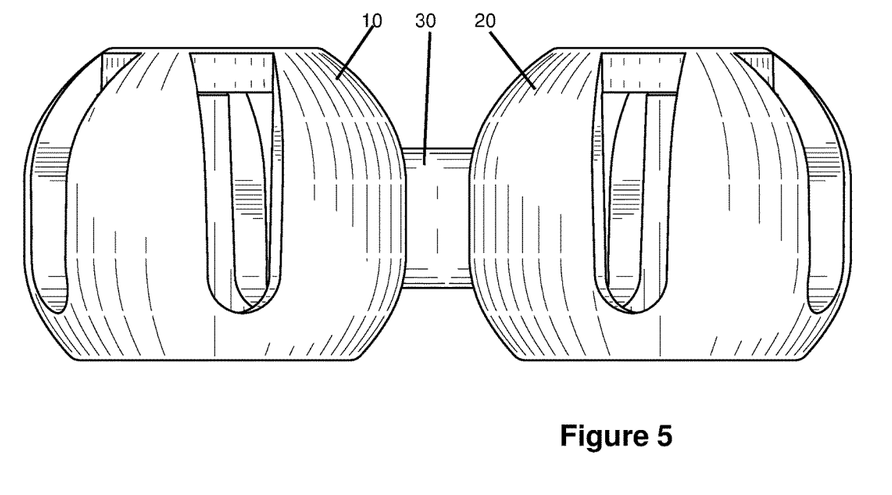
FIG. 5 shows a top view of the nasal clip of FIG. 1.
Figure 6:
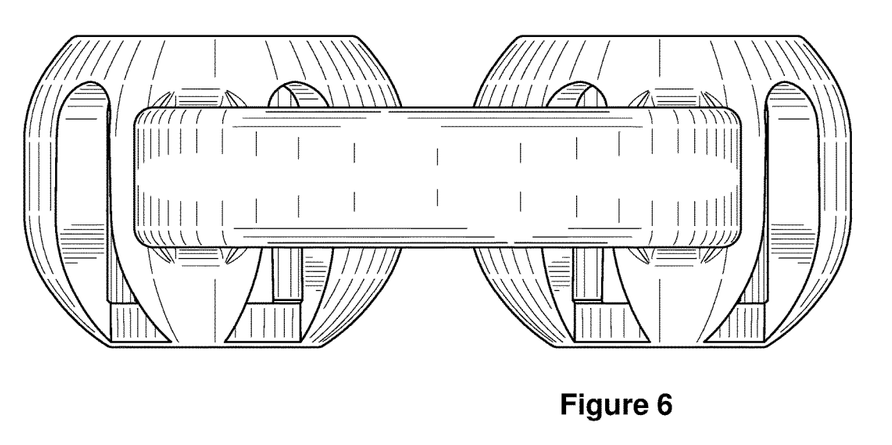
FIG. 6 shows a bottom view of the nasal clip of FIG. 1.

FIG. 5 shows a top view of the nasal clip of FIG. 1. FIG. 6 shows a bottom view of the nasal clip of FIG. 1. Note that the spheroid holders 10 and 20 are wider than the U-shaped connector such that when the device is viewed from below, one sees the spheroid holders 10 and 20 around the entirety of the region where the spheroid connectors 10/20 meet the connector.

Figure 7:
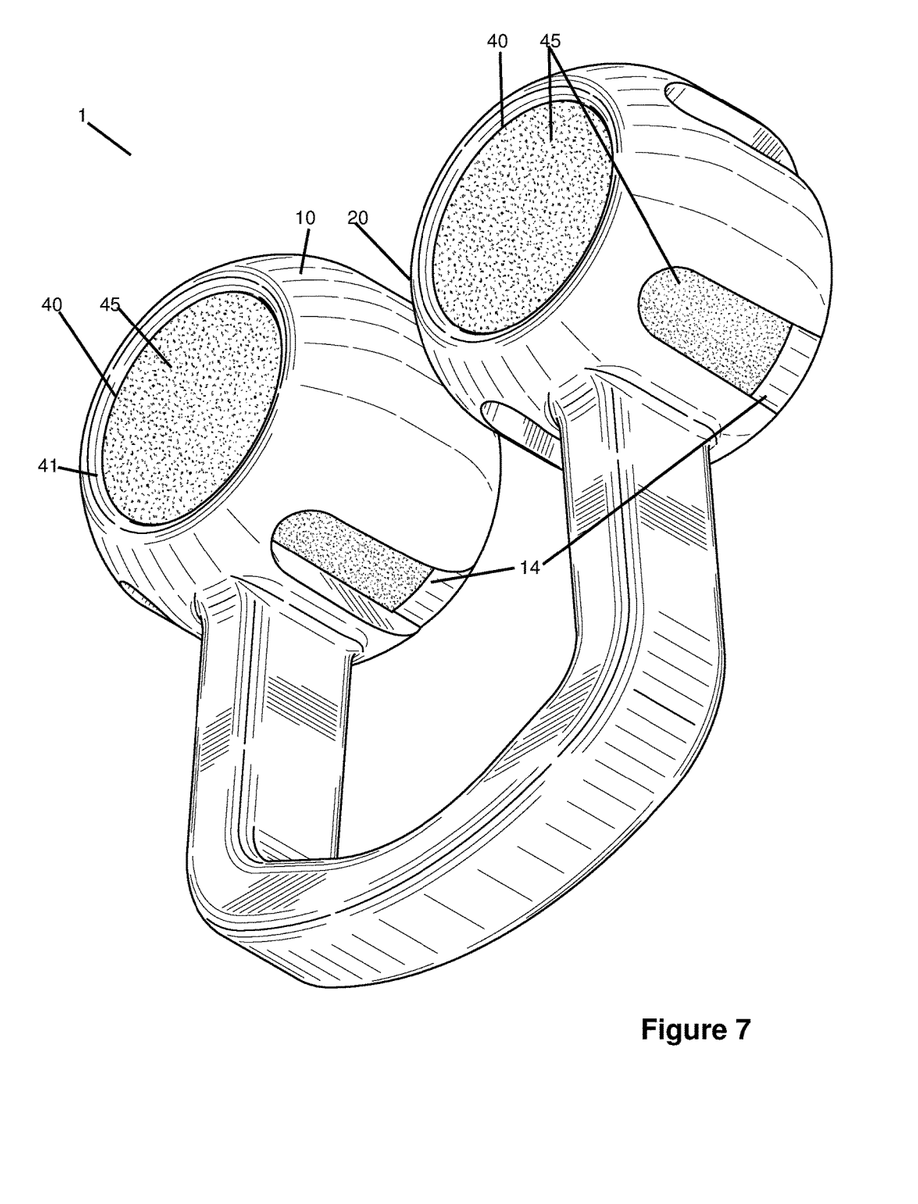
FIG. 7 shows the perspective view of the nasal clip of FIG. 1 with inserted scent balls.

FIG. 7 shows the perspective view of the nasal clip of FIG. 1 with inserted scented piece. The scented pieces 45 can be made of a plastic or resin which is permeated with an aromatic compound as is known in the art. The aromatic compounds can additionally be medicinal (have a known medical effect on the body). These pieces 45 are injected or otherwise placed inside the inner space of each spheroid holder 10 and 20. Scent exits from each respective scented piece 45 through the portals 40 and 14 of the nasal clip. The scented pieces 45 are permanently placed within the nasal clip in embodiments of the disclosed technology. When the nasal clip 1 is formed, the scent balls are placed therein and sealed with each portal being smaller in opening than an adjacent side of the scented piece, preventing the scented piece 45 from exiting there-from. For example, the front and/or back portal 40 can have an interior lip which covers an adjacent edge, corner, or closest exterior part of the scented piece 45.

Figure 8:
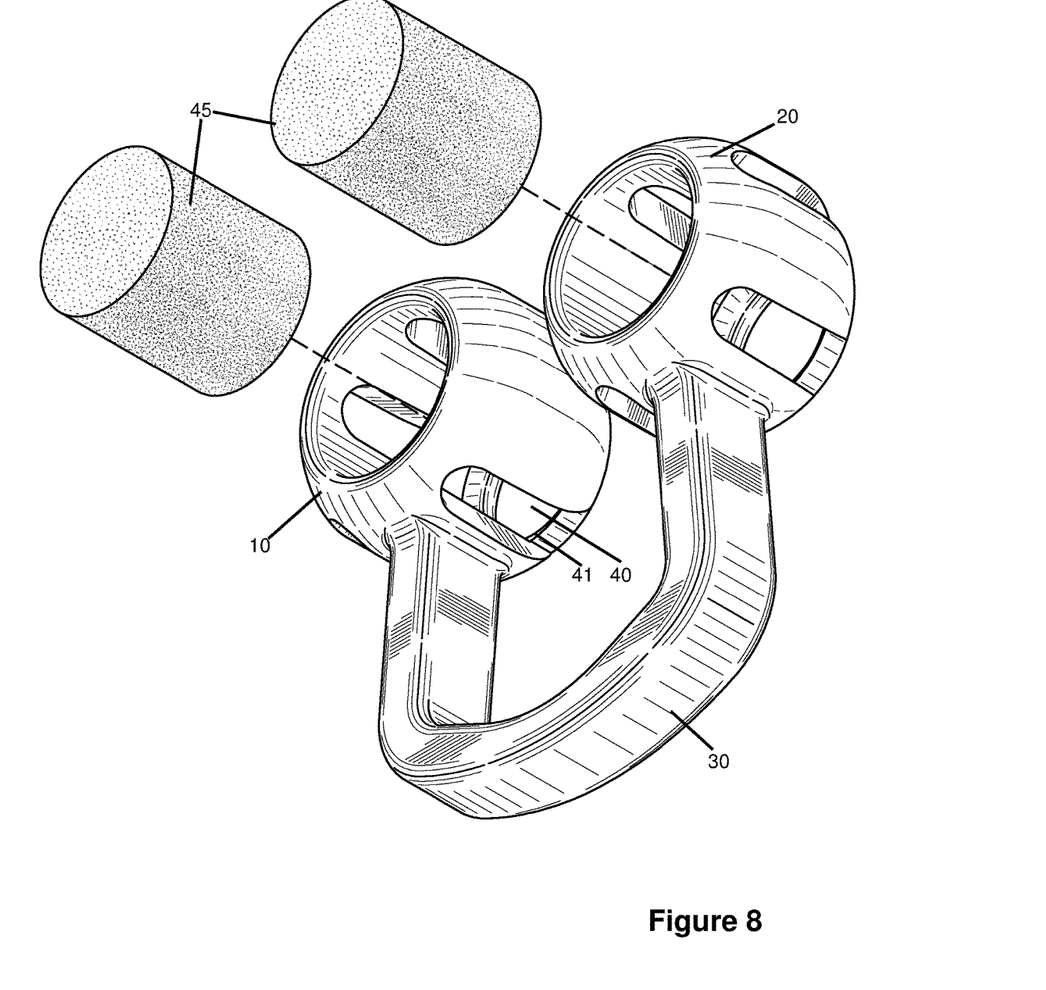
FIG. 8 shows the perspective view of the nasal clip of FIG. 7 showing the scent balls separate from the nasal clip.

FIG. 8 shows the perspective view of the nasal clip of FIG. 7 showing the scented pieces separate from the nasal clip. Here, the scented pieces 45 are each of a cylindrical shape and fit within the inner walls of the spheroid holders 10 and 20 which can have interior cylindrical walls to accommodate. The lip 41 of the portal 40 prevents the scented pieces from exiting, such as after being pressed there-into the cavity.

Figure 9:
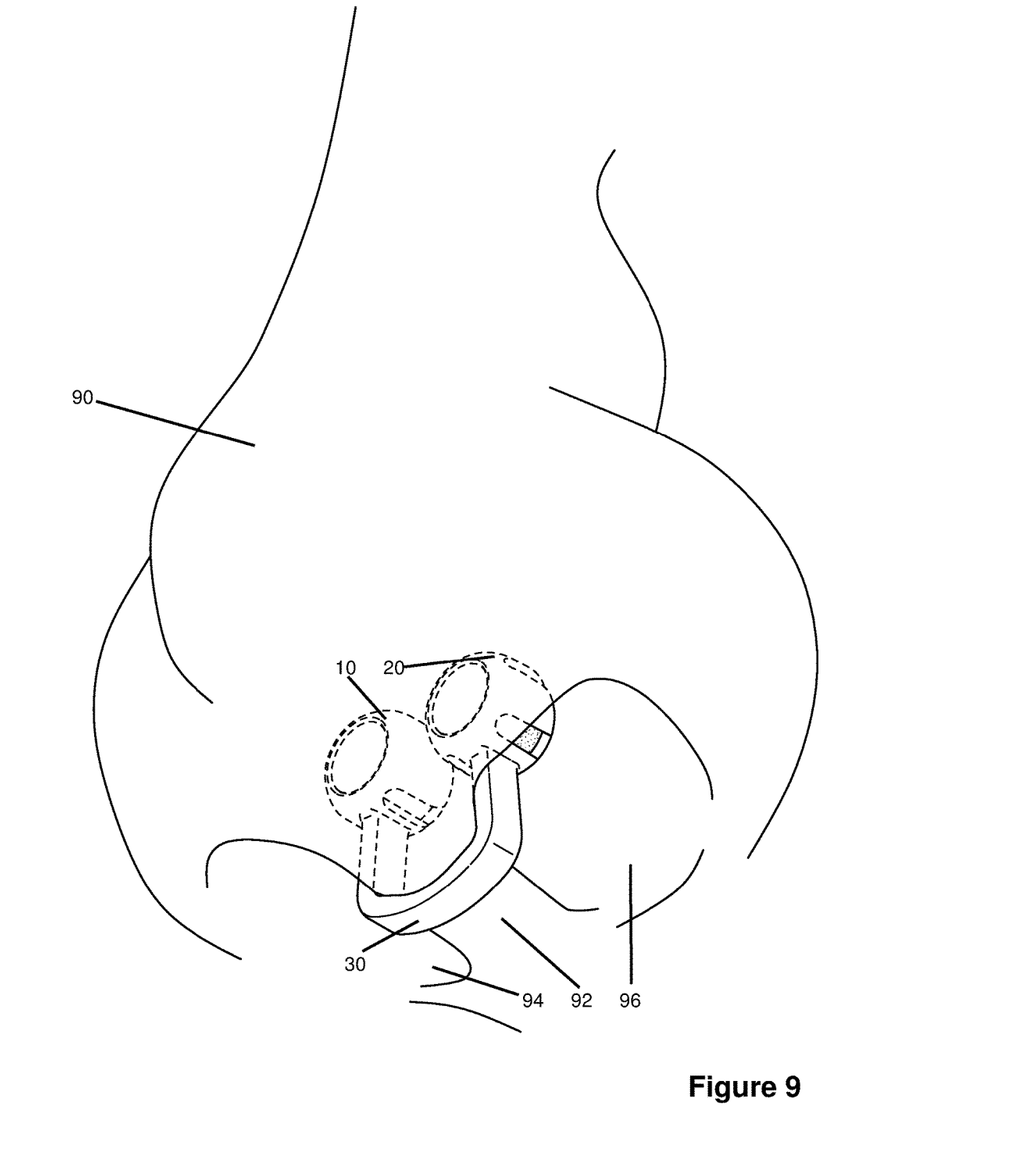
FIG. 9 shows the nasal clip of FIG. 1 inserted into a nasal cavity in an embodiment of the disclosed technology.

FIG. 9 shows the nasal clip of FIG. 1 inserted into a nasal cavity in an embodiment of the disclosed technology. The nose 90 has a bottom side 92 with a columella between two nostrils 94 and 96. The nasal clip 1 is pushed into each nostril such that the spheroid holders 10 and 20 are within the nostrils and can be in contact with a septum thereof and, in some embodiments, push on either side of the septum or columbella of the nose. The U-shaped connector is partially within the nostrils 94/96 and partially outside of the nose 90 with the middle region 30 of the U-shaped connector being outside of the nostrils. This middle region 30, which is transverse to the end regions (32 and 34) that connect to the spheroid holders 10 and 20 can be pressed against the columella.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A nasal clip and/or dilator which applies pressure to a columella of a user, comprising:
   a U-shaped base having a pair of free ends disposed to grippingly engage a nasal septum;
   two spheroid holders, one disposed at each end of said U-shaped base,
   wherein each of said two spheroid holders comprises a scented piece secured therein with an aromatic substance being inhalable through said user's nasal passages during breathing when said nasal clip is worn;
   each of said spheroid holders further comprising at least two oppositely disposed portals such that unobstructed passages are created between said scented piece and said nasal passages when said nasal clip is worn; and
   wherein said base is adapted to press upwards on said columella of said user, and
   wherein said U-shaped base engages a portion of each of said two spheroid holders, said portion being substantially equidistantly placed between said oppositely disposed portals; and wherein each of said two separate spheroid holders is formed of a circumferential wall, said
   circumferential wall comprising additional portals opening into said spherical side thereof.

2. The nasal clip of claim 1, wherein a plurality of circumferentially spaced portals open into each of said two spheroid holders further exposing said scented piece to said nasal passages.

3. The nasal clip of claim 2, wherein each said scented piece is frictionally secured in a respective said spheroid holder by way of a lip extending inward from at least one of said portals.

4. The nasal clip of claim 3, wherein each said scented piece is permanently secured in said respective said spheroid holder.

5. The nasal clip of claim 4, wherein said permanently secured nature of said spheroid holder adapts said nasal clip to be discarded after use.

6. The nasal clip of claim 1, wherein said nasal clip is substantially symmetrical about a plane extending through said U-shaped base and through said two spheroids holders.

7. A nasal clip, comprising:
   a top side, a bottom side, a front side, and a rear side, wherein, when the nasal clip is in use in a user's nose, said top side is adapted to be oriented toward the user's eyes, said bottom side is adapted to be oriented toward the user's mouth, said front side is adapted to be oriented toward a tip of the user's nose, and said back side is adapted to be oriented toward the interior of the user's head;
   two separate spheroid holders spaced apart extending to said top side;
   a U-shaped base connecting said spheroid holders extending to said bottom side, said U-shaped base engaging a portion of each of said spheroid holders, said portion being substantially equidistant between said front side and said rear side of each of said spheroid holders;
   at least one circular portal in at least one of said front side and said rear side of each spheroid holder;
   wherein said at least one circular portal comprises two circular portals, one in each of said front side and said rear side of each said spheroid holder;
   wherein each said circular portal terminates a spherical side of one of said spheroid holders and is planar with one of said front side or said rear side; and
   wherein each of said two separate spheroid holders is formed of a circumferential wall, said circumferential wall comprising additional portals opening into said spherical side thereof.

8. The nasal clip of claim 7, further comprising scent pieces, each scented piece thereof at least substantially filling a space within one of said spheroid holders.

9. The nasal clip of claim 8, wherein adjacent portions of said circumferential walls of said two separate spheroid holder, adapted to engage the nasal septum, are solid and devoid of portals, and said additional portals are situated on portions of said circumferential walls of said two separate spheroid holders which are not adapted to engage the nasal septum.

10. The nasal clip of claim 9, wherein said U-shaped base is adapted to be placed against and press upwards on a columella of a nose and each of said two separate spheroid holders is adapted to be placed against a septum of said nose.

11. A method of using said nasal clip of claim 7, comprising the steps of:
    obtaining said nasal clip with a pre-inserted aromatic scented piece in each of said two separate spheroid holders;
    placing one of said two separate spheroid holders in a first nostril and a second thereof in a second nostril.

12. The method of claim 11, further comprising a step of abutting said U-shaped base and pressing upwards against a columella.

13. The nasal clip of claim 7, wherein said nasal clip is substantially symmetrical about a plane extending through said U-shaped base and through said two spheroids holders.

14. A nasal clip comprising a U-shaped base whose ends open out into spaced apart spherical ends, each of said spherical ends having flat front and backsides and a plurality of portals adapted for escape of scent from an aromatic scented piece permanently held within each of said spherical ends,
    wherein said U-shaped base engages said spherical ends at a portion of each of said spherical ends, which portion is substantially equidistantly placed between said flat front and back sides of each of said spherical ends; and wherein each of said two separate spheroid holders is formed of a circumferential wall, said circumferential wall comprising additional portals opening into said spherical side thereof.

15. The nasal clip of claim 14, sized such that said U-shaped base is adapted to abut a columella of a nose when said each spherical end is pushed into a nostril.

16. The nasal clip of claim 15, wherein breathing through a nose causes scent to be pulled from at least one of said scented pieces.

17. The nasal clip of claim 14, wherein said plurality of portals includes a plurality of circumferential portals disposed in a circumferential wall of each said spherical end, and each of said spherical ends is devoid of said portals in a portion thereof adapted to engage the nasal septum.

* * * * *